US012564385B2

(12) United States Patent
White et al.

(10) Patent No.:     US 12,564,385 B2
(45) Date of Patent:          Mar. 3, 2026

(54) ULTRASOUND PARAMETER SELECTION USING RF DATA

(71) Applicant: FUJIFILM SONOSITE, INC., Bothell, WA (US)

(72) Inventors: Chris White, Vancouver (CA); Stanley Poon, Thornhill (CA); Alex Forbrich, Bothell, WA (US); Connor Sousa, North York (CA); Andrew Needles, Toronto (CA)

(73) Assignee: FUJIFILM SONOSITE, INC., Bothell, WA (US)

( * ) Notice: Subject to any disclaimer, the term of this patent is extended or adjusted under 35 U.S.C. 154(b) by 93 days.

(21) Appl. No.: 18/542,493

(22) Filed: Dec. 15, 2023

(65) Prior Publication Data

US 2025/0195042 A1     Jun. 19, 2025

(51) Int. Cl.
*A61B 8/00*          (2006.01)
*G01S 7/52*          (2006.01)

(52) U.S. Cl.
CPC .............. *A61B 8/54* (2013.01); *A61B 8/4444* (2013.01); *A61B 8/461* (2013.01); *A61B 8/469* (2013.01); *A61B 8/5207* (2013.01); *A61B 8/5223* (2013.01); *G01S 7/5205* (2013.01)

(58) Field of Classification Search
CPC ......... A61B 8/54; A61B 8/4444; A61B 8/461; A61B 8/469; A61B 8/5207; A61B 8/5223; G01S 7/5205
See application file for complete search history.

(56) References Cited

U.S. PATENT DOCUMENTS

2016/0249886 A1*  9/2016  Sakaguchi ............... A61B 8/56
                                                                600/437
2017/0143312 A1*  5/2017  Hedlund ................ A61B 6/487
2020/0196987 A1*  6/2020  Kim ................... G01S 7/52049

* cited by examiner

*Primary Examiner* — Michael J Carey
*Assistant Examiner* — Zainab Mohammed Aldarraji
(74) *Attorney, Agent, or Firm* — Womble Bond Dickinson (US) LLP

(57)          ABSTRACT

Ultrasound systems, methods and other apparatuses for ultrasound parameter selection are disclosed. In some embodiments, the ultrasound system includes a processor system implemented to generate ultrasound images based on the sampled data and candidate sound speeds, generate image scores for the ultrasound images, and determine the speed-of-sound values from the candidate sound speeds based on a ranking of the ultrasound images according to the image scores.

20 Claims, 12 Drawing Sheets

<u>100</u>

500

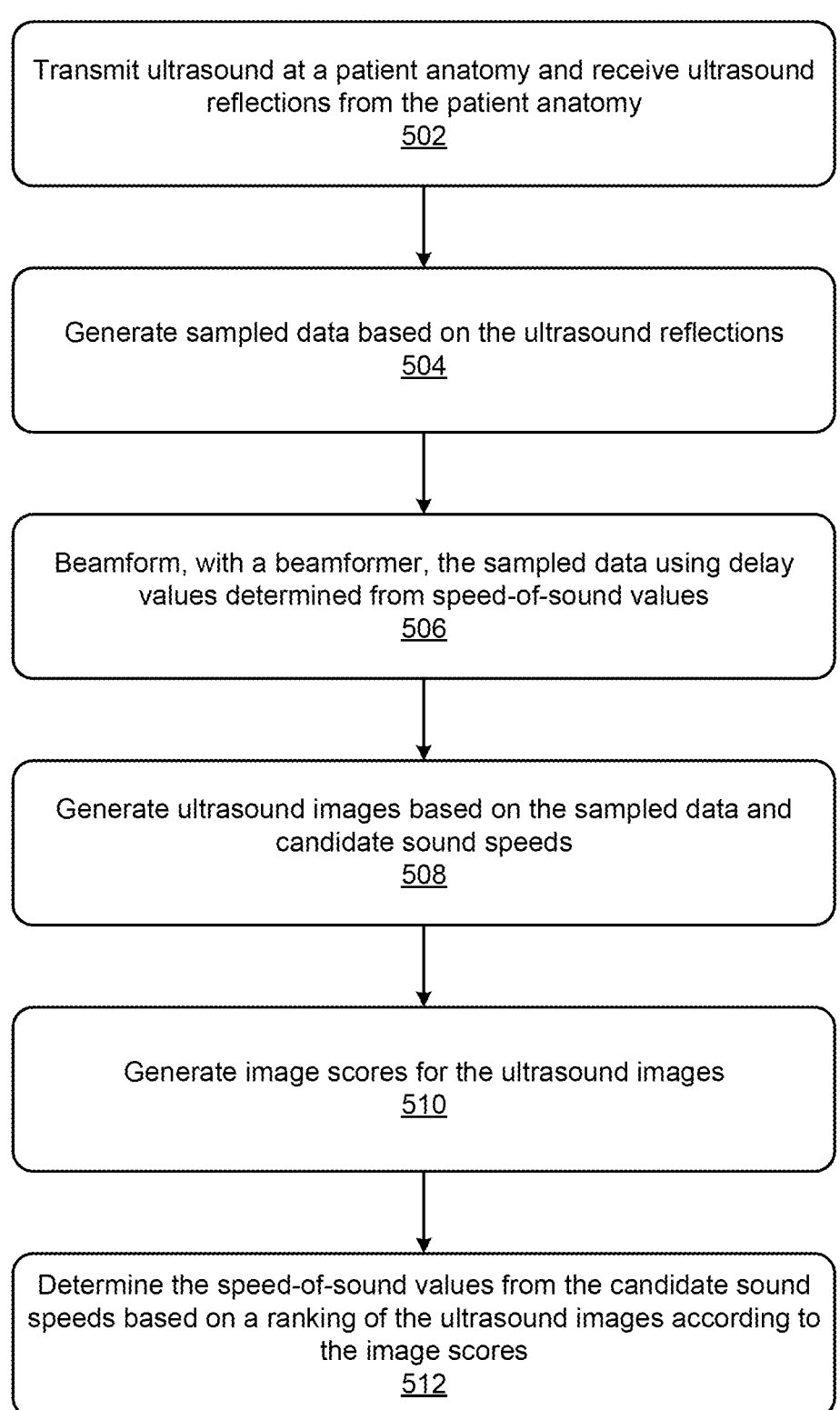

Transmit ultrasound at a patient anatomy and receive ultrasound reflections from the patient anatomy
502

Generate sampled data based on the ultrasound reflections
504

Beamform, with a beamformer, the sampled data using delay values determined from speed-of-sound values
506

Generate ultrasound images based on the sampled data and candidate sound speeds
508

Generate image scores for the ultrasound images
510

Determine the speed-of-sound values from the candidate sound speeds based on a ranking of the ultrasound images according to the image scores
512

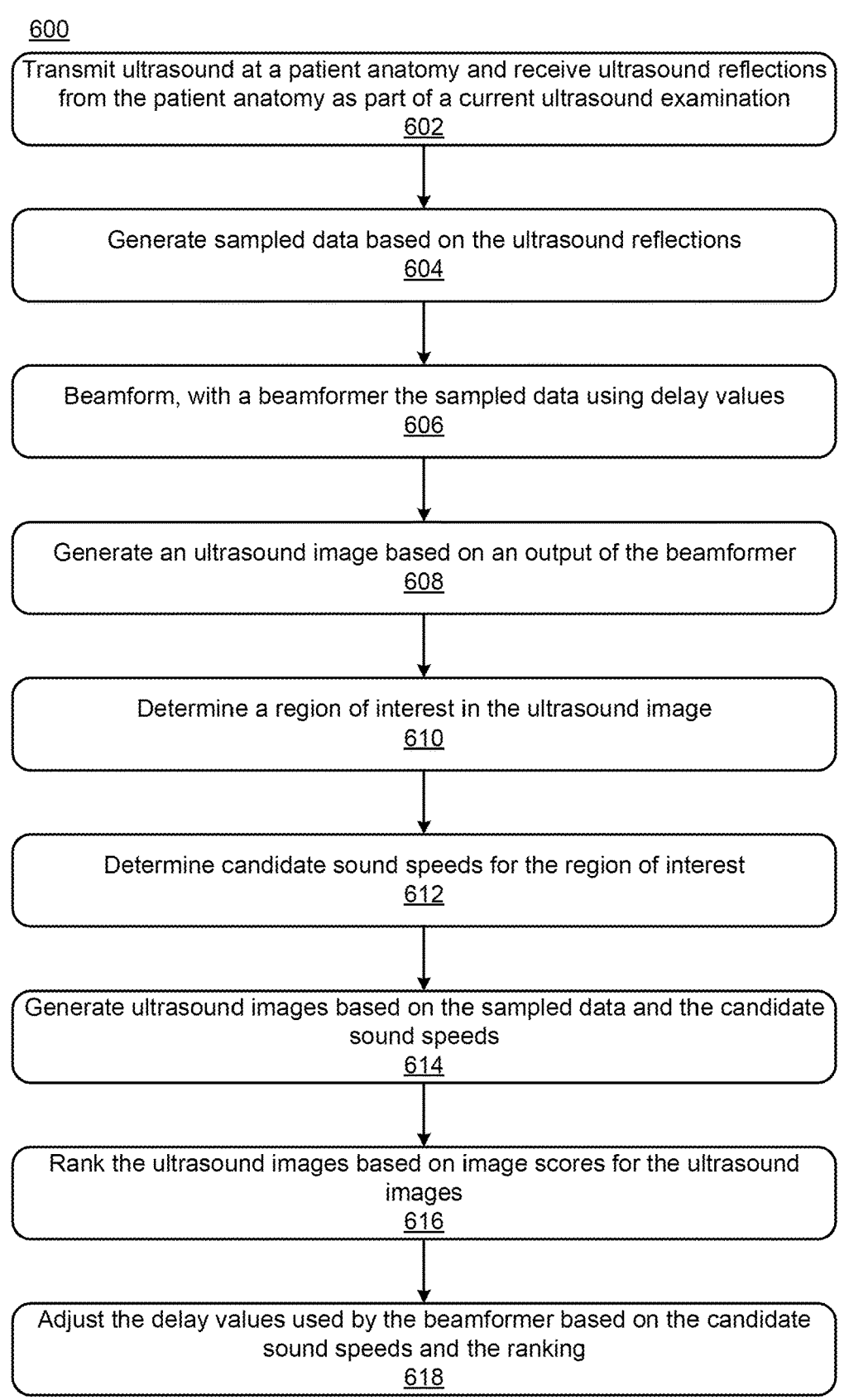

Transmit ultrasound at a patient anatomy and receive ultrasound reflections from the patient anatomy as part of a current ultrasound examination
602

Generate sampled data based on the ultrasound reflections
604

Beamform, with a beamformer the sampled data using delay values
606

Generate an ultrasound image based on an output of the beamformer
608

Determine a region of interest in the ultrasound image
610

Determine candidate sound speeds for the region of interest
612

Generate ultrasound images based on the sampled data and the candidate sound speeds
614

Rank the ultrasound images based on image scores for the ultrasound images
616

Adjust the delay values used by the beamformer based on the candidate sound speeds and the ranking
618

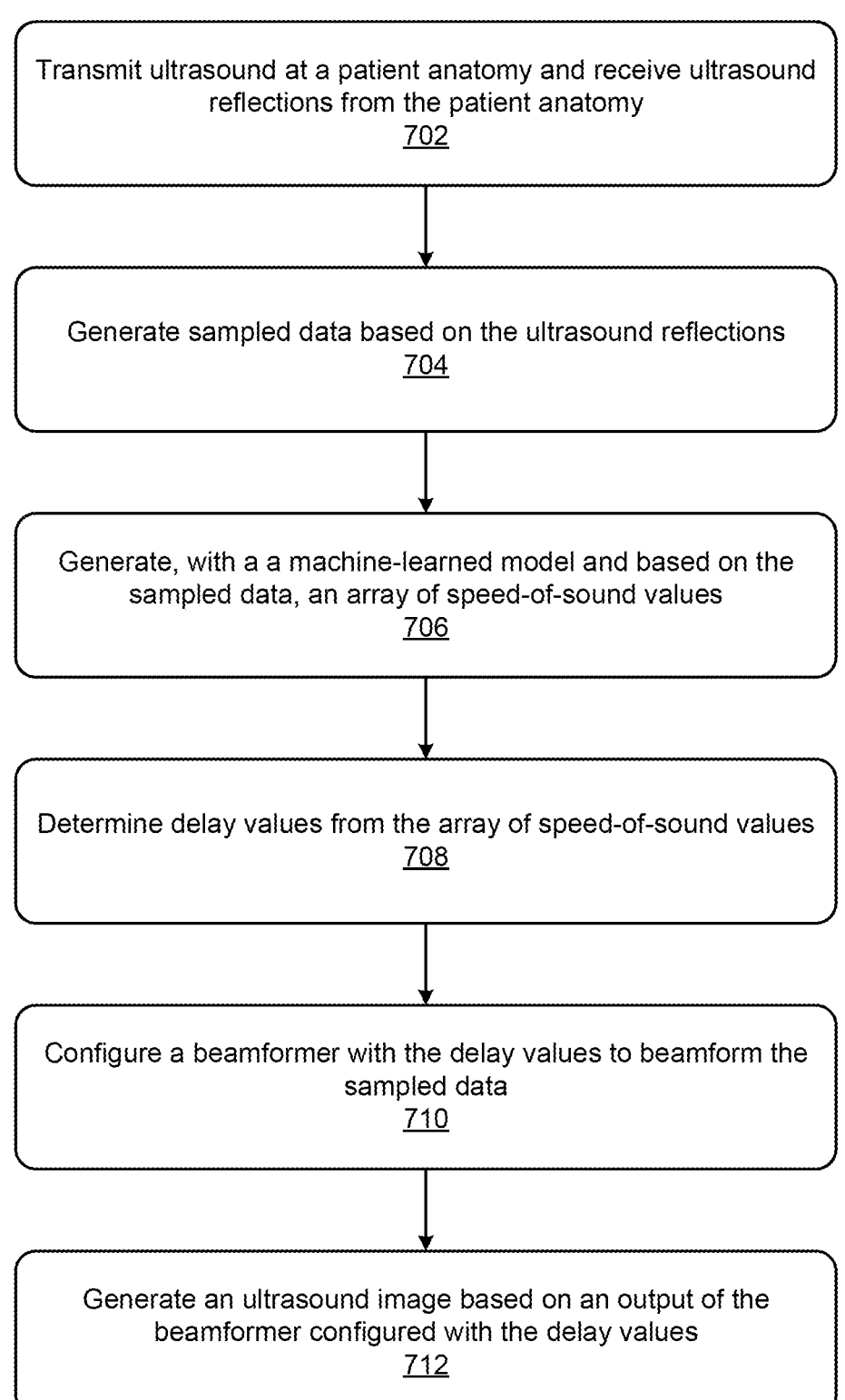

Transmit ultrasound at a patient anatomy and receive ultrasound reflections from the patient anatomy
702

Generate sampled data based on the ultrasound reflections
704

Generate, with a a machine-learned model and based on the sampled data, an array of speed-of-sound values
706

Determine delay values from the array of speed-of-sound values
708

Configure a beamformer with the delay values to beamform the sampled data
710

Generate an ultrasound image based on an output of the beamformer configured with the delay values
712

ULTRASOUND PARAMETER SELECTION USING RF DATA

FIELD OF THE INVENTION

Embodiments disclosed herein relate to ultrasound systems. More specifically, embodiments disclosed herein are related to ultrasound parameter selection using radio-frequency (RF) data for use with an ultrasound machine.

BACKGROUND

Ultrasound systems can generate ultrasound images by transmitting sound waves at frequencies above the audible spectrum into a body, receiving echo signals caused by the sound waves reflecting from internal body parts, and converting the echo signals into electrical signals for image generation. Because they are non-invasive and non-ionizing, ultrasound systems are used ubiquitously. However, conventional ultrasound systems can be limited in their effectiveness because they utilize parameter values that are often pre-selected prior to an ultrasound examination, or that are poor estimates of true or optimum values. For example, beamformers are used to focus ultrasound transmission and/or reception at a target anatomy and often are implemented with delay computations that are based on a single, poor estimate of the speed of sound. Sometimes the delay values are not even estimated based on ultrasound data, but are set to a default, assumed value. As a result, the ultrasound beam may not be properly focused, which can reduce the signal-to-noise ratio and/or introduce interference for the ultrasound data used in image generation.

In another example, noise power estimates may not be data driven, and the beamformer may not be controlled by the noise power estimate, or be controlled by a poor noise power estimate, which can cause severe issues when transducer elements are faulty. In yet another example, imaging parameter values (e.g., gain, depth, etc.) can be merely pre-selected for an examination type, and used throughout an ultrasound examination, even when the anatomy being imaged does not correspond to the selected examination type. In still another example, the transducer selection itself can be based on availability/convenience, rather than a desired property about the ultrasound data.

In cases where the ultrasound systems do provide mechanisms for adjustment, data-driven estimates are often based on data that has been heavily processed (e.g., filtered and decimated) and thus has lost information-theoretic value. Hence, the parameter estimates may be poor. Therefore, the patient may not receive the best care possible.

SUMMARY

Ultrasound systems, methods and apparatuses for ultrasound parameter selection are disclosed. In some embodiments, the ultrasound system includes an ultrasound probe configured to transmit ultrasound at a patient anatomy and receive ultrasound reflections from the patient anatomy, one or more analog-to-digital converters configured to generate sampled data based on the ultrasound reflections, and a beamformer configured to beamform the sampled data using delay values determined from speed-of-sound values. The ultrasound system also includes a processor system implemented to generate ultrasound images based on the sampled data and candidate sound speeds, generate image scores for the ultrasound images, and determine the speed-of-sound values from the candidate sound speeds based on a ranking of the ultrasound images according to the image scores.

In some other embodiments, an ultrasound system includes an ultrasound probe configured to transmit ultrasound at a patient anatomy and receive ultrasound reflections from the patient anatomy as part of a current ultrasound examination, one or more analog-to-digital converters configured to generate sampled data based on the ultrasound reflections, a beamformer configured to beamform the sampled data using delay values, and an image generation circuit configured to generate an ultrasound image based on an output of the beamformer. The ultrasound system also includes a processor system implemented to determine a region of interest in the ultrasound image, determine candidate sound speeds for the region of interest, generate ultrasound images based on the sampled data and the candidate sound speeds, rank the ultrasound images based on image scores for the ultrasound images, and adjust the delay values used by the beamformer based on the candidate sound speeds and the ranking.

In yet some other embodiments, an ultrasound system includes an ultrasound probe configured to transmit ultrasound at a patient anatomy and receive ultrasound reflections from the patient anatomy and one or more analog-to-digital converters configured to generate sampled data based on the ultrasound reflections. The ultrasound system also includes a processor system configured to implement a machine-learned model to generate, based on the sampled data, an array of speed-of-sound values, determine delay values from the array of speed-of-sound values, and configure a beamformer with the delay values to beamform the sampled data. The ultrasound system additionally includes an image generation circuit implemented to generate an ultrasound image based on an output of the beamformer configured with the delay values.

BRIEF DESCRIPTION OF THE DRAWINGS

The appended drawings illustrate examples and are, therefore, exemplary embodiments and not considered to be limiting in scope.

FIG. 5 illustrates a first example method that can be implemented by an ultrasound system in accordance with some embodiments.

FIG. 6 illustrates a second example method that can be implemented by an ultrasound system in accordance with some embodiments.

FIG. 7 illustrates a third example method that can be implemented by an ultrasound system in accordance with some embodiments.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Systems, devices, and techniques are disclosed herein for ultrasound parameter selection using radio-frequency (RF) data (e.g., received ultrasound data that has been digitized but may not be processed, such as beamformed, filtered, decimated, etc.). RF data can also be referred to as raw (unprocessed) sampled data. Hence, the RF data used for ultrasound parameter selection maintains maximum information-theoretic value. The RF data can be processed in real time, for example to produce a B-Mode or Color Doppler image, so that results can be used in a current ultrasound examination. Even so, the raw, unprocessed data is maintained and can be processed (or reprocessed) for ultrasound parameter selection or for other purposes, such as those described herein, for the current ultrasound examination or a subsequent ultrasound examination. The techniques described herein can be used for both pre-clinical and clinical systems. An example embodiment described throughout this disclosure includes the estimation of speed-of-sound (SoS) parameters that can be used to configure a beamformer (e.g., by setting beamformer delays based on the SoS estimate(s)). However, the techniques described herein are not so limited and can be used for any suitable type of ultrasound parameter estimation, including, but not limited to, noise-power estimation and beamformer control therefrom, imaging-parameter estimation, transducer emulation and recommendation, and the like.

Figure 1:
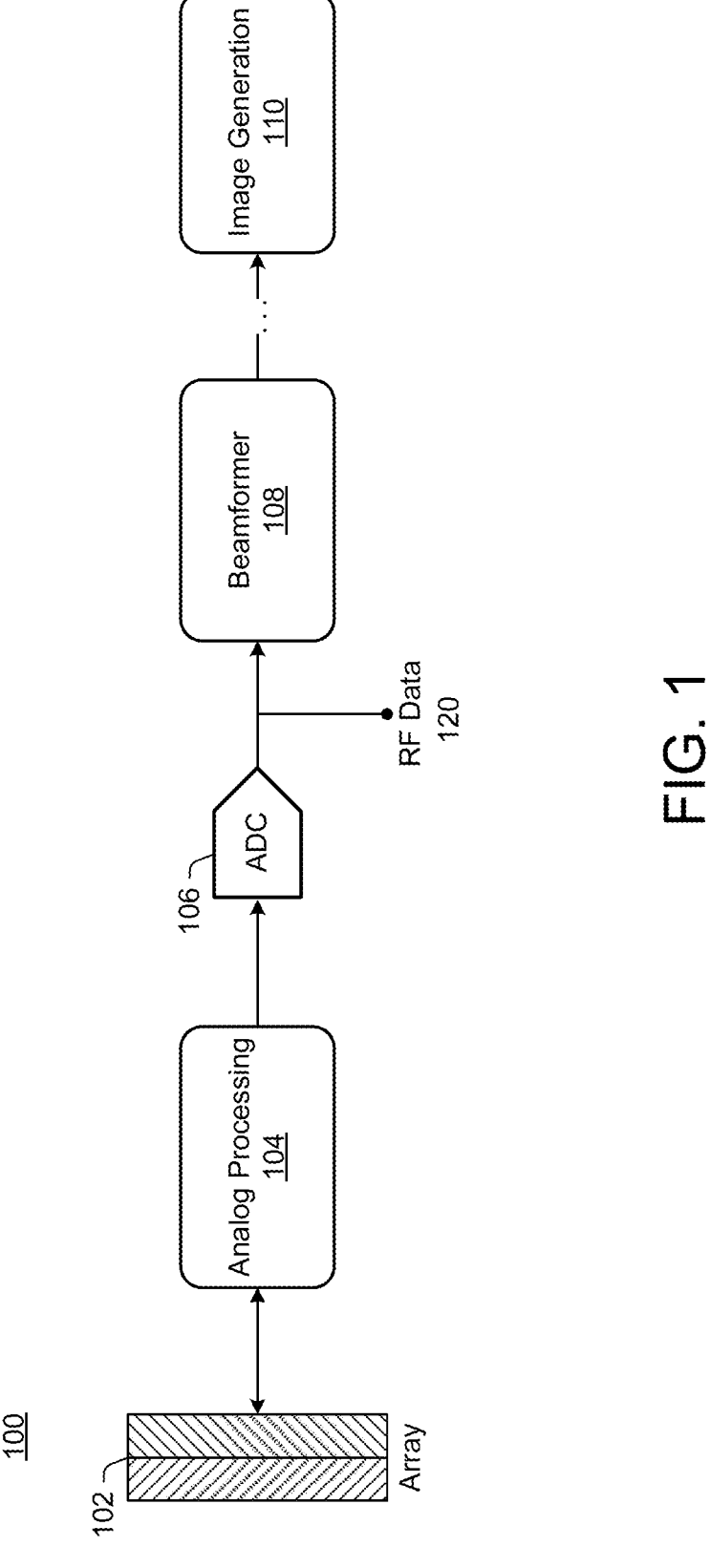
FIG. 1 illustrates radio-frequency (RF) data capture in the signal processing chain of an ultrasound system.

FIG. 1 illustrates RF data capture in the signal processing chain 100 of an ultrasound system. Referring to FIG. 1, the signal processing chain 100 includes components of a receiver configured to receive reflected ultrasound from a patient anatomy. The reflected ultrasound signals are received at an ultrasound array 102 and converted to electrical signals that are processed in the analog domain by the analog processing block 104. The analog processing block 104 can include any suitable analog processing components, such as amplifiers, attenuators, switches, multiplexors, gain control, anti-aliasing filters, and generally any circuitry to isolate the electrical signals and condition them for sampling by the analog-to-digital converter (ADC) 106. The ADC 106 samples the output of the analog processing block 104 and generates discrete time, quantized samples. The ADC 106 can be free-running or controlled by a clock circuit in a control loop (not shown for clarity) and can generate samples of any suitable size (e.g., bit precision), such as, for example, 12-bit samples at 20 MHz rate. The samples output by the ADC 106 are captured and referred to as RF data or sampled data, which can be used for ultrasound parameter selection in accordance with embodiments described herein.

The samples output by the ADC 106 are supplied to a beamformer 108 that can sum delayed sample values corresponding to different transducer elements to spatially focus the receiver towards a desired direction, such as at a patient anatomy. The beamformer itself can reside on the acquisition hardware directly (e.g., FPGA, etc.) or be implemented on a processor such as a Graphics Processing Unit (GPU) on a separate processing device which may also be the primary control Central Processing Unit (CPU) (e.g., a system computer, etc.). The beamformed data is supplied to an image generation block 110 that can generate an ultrasound image.

Since the RF data 120 has not been processed (e.g., filtered, decimated, beamformed, etc.) by the digital signal processing in the receiver, the RF data 120 contains maximum information-theoretic value and can be used for ultrasound parameter selection, such as, for example, for estimating one or more values of the SoS. In some embodiments, the RF data 120 is captured via a channel of the ultrasound system that is dedicated to ultrasound parameter selection and whose output is not directly used for image generation. For instance, the channel can correspond to dedicated transducer elements and can use an ADC precision that is different than that for other channels used for image generation. For example, the channel can use 8-bit data while the other channels use 12-bit data for image generation. In another example, the channel can use 12-bit data while the other channels use 8-bit data for image generation.

Further, although the examples described herein generally refer to setting beamformer delays for ultrasound reception, one skilled in the art would understand how to apply aspects of the techniques disclosed herein to setting beamformer delays for ultrasound transmission.

Figure 2:
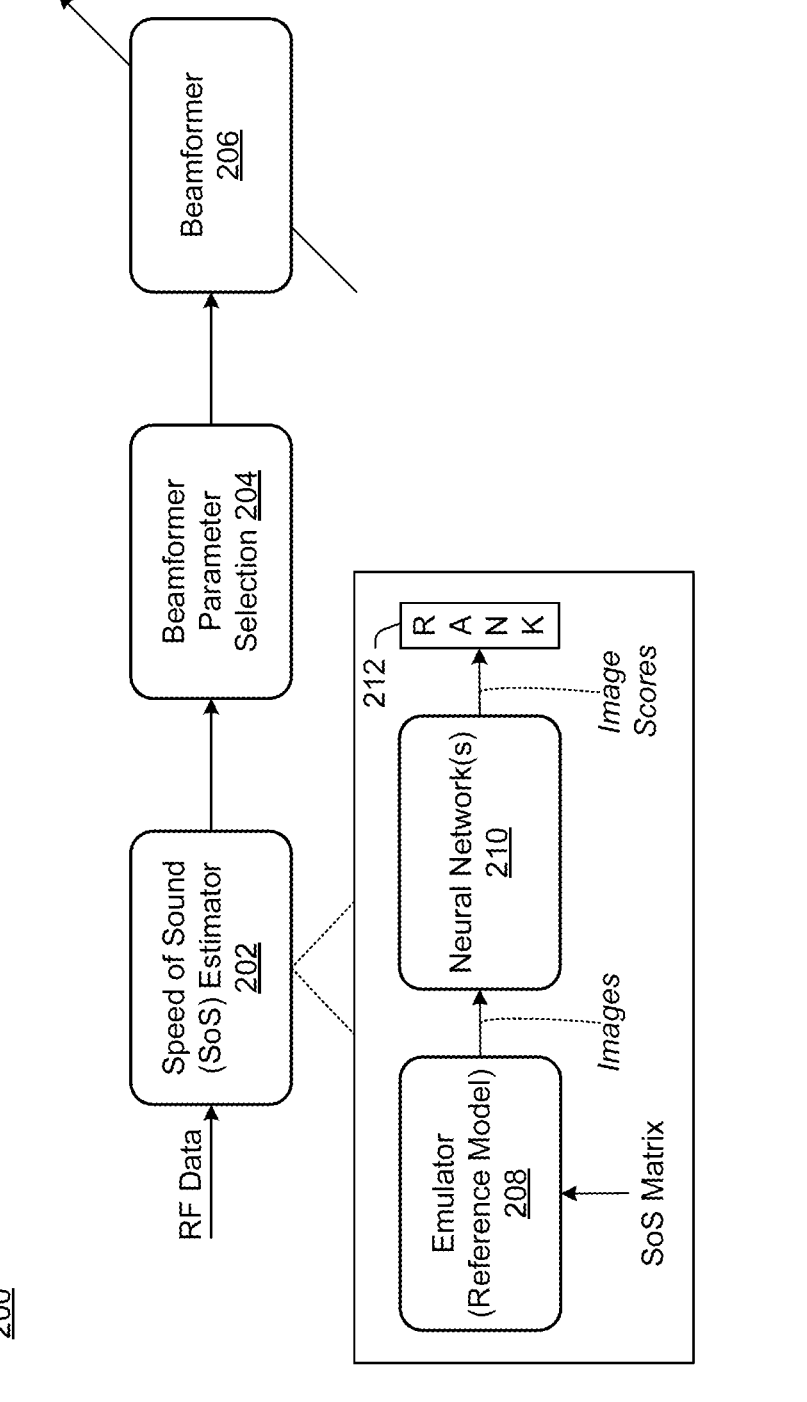
FIG. 2 illustrates components of an ultrasound system for speed-of-sound (SoS) parameter selection in accordance with some embodiments.

FIG. 2 illustrates components of an ultrasound system at 200 for SoS parameter selection in accordance with some embodiments. The system in FIG. 2 includes a SoS estimator block 202, a beamformer parameter selection block 204, and a beamformer 206 having configurable delays that can be set based on one or more SoS values determined by the system. In an example, the beamformer 206 includes configurable gains (e.g., amplifiers and/or attenuators) that can be set based on one or more SoS values determined by the system. The system in FIG. 2 also illustrates an example of the SoS estimator block 202 that includes an emulator (e.g., reference model) 208, one or more neural networks 210, and a rank block 212 that can rank images generated by the emulator 208 according to their scores generated by the neural network 210.

The emulator 208 can implement any suitable emulation circuitry that can emulate, copy, approximate, simulate, etc., the function of the digital receiver circuitry in FIG. 1, e.g., the beamformer 108 and the image generation block 110. The emulator 208 can be implemented in hardware, software, firmware, processing logic, GPU (Graphics Processing Unit), etc., and combinations thereof. In some embodiments, the emulator 208 receives an SoS matrix (or array) that includes one or more values of the SoS. For instance, the SoS matrix can be supplied by a database of SoS matrices (not shown in FIG. 2 for clarity, and discussed in more detail with respect to FIG. 3). In some embodiments, the SoS matrix supplied to the emulator 208 is an SoS matrix determined from a previous ultrasound examination.

The SoS matrix can include any suitable number of values in any suitable format. In some embodiments, the SoS matrix includes a vector having elements corresponding to lines of ultrasound, so that each line of ultrasound is associated with its own value of the SoS. The SoS matrix can include multiple vectors for each ultrasound line, so that a suitable SoS value for each ultrasound line can be determined. Additionally or alternatively, the SoS matrix can include SoS values for each delay of the beamformer, so that the SoS can be adjusted across the entire ultrasound image generated by the image generation block 110. In some embodiments, a user defines a region of interest in an ultrasound image generated by the image generation block, and the SoS matrix can include SoS values for pixels corresponding to the region of interest, so that the SoS can be optimized for the region of interest (e.g., to maximize the contrast in the region of interest). In some embodiments, SoS values for parts of the ultrasound image that do not belong to the region of interest are not included in the SoS matrix. Hence, the SoS values for the region of interest can be optimized for the region of interest without being biased by other parts of the ultrasound image.

In operation, in some embodiments the emulator 208 generates ultrasound images based on different values of the SoS parameter in the SoS matrix, and the SoS values are used to set beamformer delay values in the emulator used to generate the images. For instance, for each ultrasound line, multiple SoS values can be used in the emulator 208 to generate multiple images. In some embodiments, SoS values for multiple lines are used to generate each new ultrasound image. For example, each ultrasound image generated by the emulator can correspond to a different SoS value for all lines. In some other embodiments, each ultrasound image generated by the emulator can correspond to a different SoS value for only one line at a time. In some other embodiments, each ultrasound image can correspond to a different arrangement of SoS values that correspond to a region of interest.

In some embodiments, the images generated by the emulator (e.g., reference model) 208 are processed by the neural network 210, which is trained to generate image scores for each image (e.g., image quality scores). The image scores can be based on contrast, so that an image with a higher contrast can receive a higher image score. Additionally or alternatively, the image score can be based on a combination of any suitable image properties, such as amount of noise, edge sharpness, amount of speckle, anatomy content, field of view, contrast to noise ratio, or user-supplied quality score, etc.

Based on the image scores, the rank block 212 ranks the ultrasound images generated by the emulator 208. In some embodiments, the SoS values used to generate the ultrasound image with the highest image score are provided from the SoS estimator block 202 to the beamformer parameter selection block 204, which configures the delays of the beamformer 206 based on the SoS values determined by the SoS estimator block 208 via the emulator 208, neural network 210, and rank block 212. In some embodiments, the beamformer 206 includes programmable gains (e.g., each delay can include a gain, amplifier, attenuator, on/off switch, and the like). When the system determines that the SoS value for that delay corresponds to an air bubble, the gain is attenuated. More specifically, if there are air bubbles causing a strong reflection, it is desirable to lower the gain to compensate. In such case, in some embodiments, the system examines both the signal amplitude and estimates SoS to determine where to attenuate gain. The SoS value can be a threshold (e.g., a significant deviation from tissue).

Figure 3:
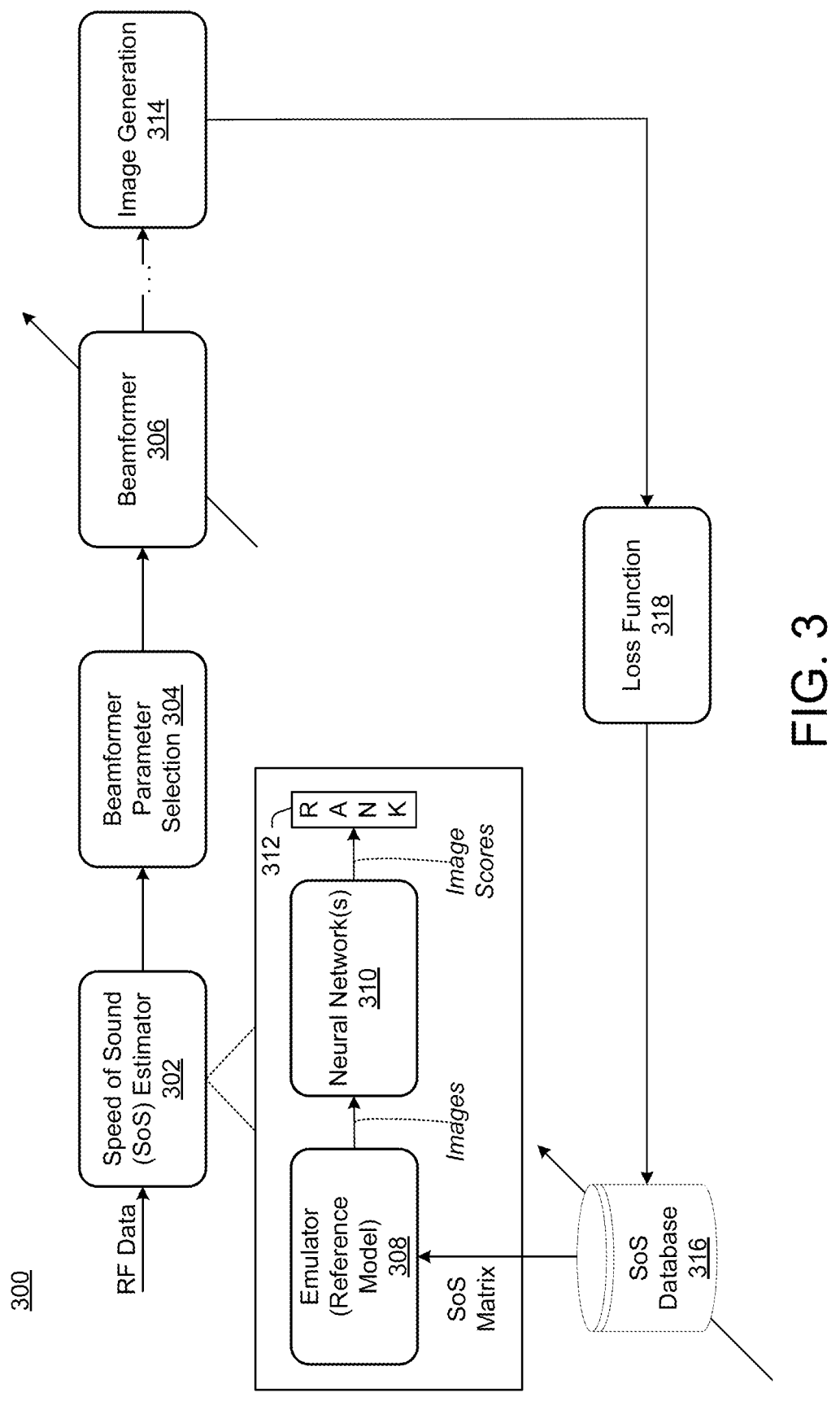
FIG. 3 illustrates components of an ultrasound system for adaptive SoS parameter selection in accordance with some embodiments.

FIG. 3 illustrates components of an ultrasound system for adaptive SoS parameter selection in accordance with the present invention. Referring to FIG. 3, the system 300 includes a SoS estimator block 302 (which is an example of the SoS estimator block 202), a beamformer parameter selection block 304 (which is an example of the beamformer parameter selection block 204), and a beamformer 306 having configurable delays (which is an example of the beamformer 206).

In some embodiments, the SoS estimator block 302 includes an emulator (e.g., reference model) 308 (which is an example of the emulator 208), one or more neural networks 310 (which is an example of the neural network(s) 210), and a rank block 312 (which is an example of the rank block 212). In some embodiments, the system at FIG. 3 also includes an image generation block 314 (which is an example of the image generation block 110 in FIG. 1), a SoS database 316, and a loss function 318.

In operation, in some embodiments, the system at FIG. 3 adapts the SoS values that are maintained in the database 316 that supplies one or more SoS matrices to the emulator 308. For instance, the image generation block 314 can generate an ultrasound image that includes a region having expected values (e.g., known pixel values), such as a black region, a white region, etc. To the extent that the pixels in the region differ from their expected values (e.g., of black or white), the loss function 318 can adjust one or more SoS values maintained in the database 316. In some embodiments, an initial value of the SoS matrix supplied from the database 316 to the emulator 308 (e.g., before the SoS matrix is adjusted during a current ultrasound examination based on the loss function 318) is obtained from a previous ultrasound examination. For instance, the initial value of the SoS matrix for the current ultrasound examination can correspond to a final value of the SoS matrix from the previous ultrasound examination. The previous ultrasound examination can correspond to the same examination type as the current ultrasound examination and be selected based on this same examination type. Hence, the database 316 can maintain multiple SoS matrices that correspond to different examination types, anatomies, ultrasound frequencies, ultrasound scanner (probe) types and model numbers, ultrasound operators, patients, etc. One or more of these parameters can be used to select the initial SoS matrix supplied from the database 316 to the emulator 308. In some embodiments, the initial SoS matrix is populated with a value of 1540 m/s for at least one SoS value. In some embodiments, the initial SoS matrix is populated with a value of 1540 m/s for all SoS values.

In some embodiments, an initial value of the SoS matrix is populated with a single measured value of the SoS. For example, all values of the initial SoS matrix can be set to the single measured value of the SoS. The single measured value can be determined in any suitable way, such as via direct estimation of the SoS, e.g., using pulse-echo ultrasound, as described in Anderson, et al., "The Direct Estimation of Sound Speed Using Pulse-Echo Ultrasound," Journal of the Acoustical Society of America. 104, 3099-106. 10.1121/1.423889 (1998).

The system can update the SoS values in the database 316 in any suitable way. In embodiments, the system updates the SoS matrix maintained by the database 316 on a line-by-line basis. For instance, the system can determine one or more SoS values for an ultrasound line at a first iteration, and at a subsequent iteration, can determine one or more SoS values for another ultrasound line. In some embodiments, the SoS values for one ultrasound line are determined based on SoS values for another ultrasound line. For instance, an SoS value for a first line can be determined as the sum of an SoS value for a second line plus an offset value. The offset value can be determined in any suitable way, such as by adding or subtracting a small number, and the addition or subtraction can be based on whether or not the ultrasound line crosses a tissue boundary. In some embodiments, the offset is zero, so that SoS value for the first and second lines are equal. In some embodiments, the offset is added and/or subtracted according to a pattern. The pattern can be set so that a percentage of all possible SoS matrices are tried. Additionally or alternatively, the pattern can be biased so that certain types of SoS values are tried before other types of SoS values, such as by trying offsets clustered around 1540 m/s before trying other clusters of SoS values. Note that the system does not need to update the entire SoS matrix at one time and can perform the update over time, e.g., by updating some, but not all, SoS values of the matrix at each iteration.

Additionally or alternatively, the SoS value for one ultrasound line can be determined from the SoS values from two other ultrasound lines, such as by interpolating between the lines or by averaging the SoS values from the other two lines to determine the SOS value for the one ultrasound line. In some embodiments, the system updates the SoS matrix maintained by the database 316 based on a genetic algorithm. In some embodiments, the system updates the SoS matrix maintained by the database 316 based on a greedy algorithm. In some embodiments, the system updates the SoS matrix maintained by the database 316 based on a random number generator. For example, the SoS values in the SoS matrix used for an iteration can be randomly generated from a random number generator. The SoS values can be independent and identically distributed. In some embodiments, the SoS values are biased around a mean and constrained to be within a range.

By adapting the SoS values and/or maintaining different sets of values for one or more SoS matrices, the ultrasound system can utilize different SoS values at different times. For example, with different SoS values for different tissue types, in some embodiments, the ultrasound system changes the SoS value(s) being used based on the tissue type being imaged (e.g., uses different SoS values when imaging bone tissue, fat tissue, organ tissue, etc.). In some embodiments, the ultrasound system segments different portions of the anatomy while imaging and then reprocesses the data using the SoS value associated with the individual anatomy segment.

Figure 4:
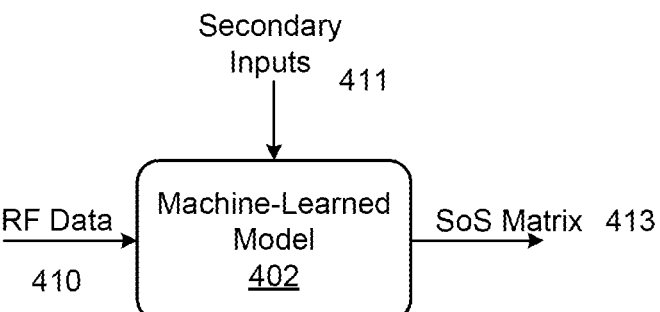
FIG. 4 illustrates a machine-learned model for a SoS parameter selection in accordance with some embodiments.

FIG. 4 illustrates a machine-learned model 402 for SoS parameter selection in accordance with some embodiments. The machine-learned model 402 is an example of the SoS estimator 202 in FIG. 2 and can include any suitable component, such as one or more neural networks that are trained to generate a SoS matrix based on RF data. The machine-learned model 402 can include a neural network configured to determine one or more anatomies, another neural network configured to identify tissue boundaries, and another neural network trained to generate the SoS matrix based on the determined anatomies and tissue boundaries. For example, in some embodiments, the machine-learned model 402 segments out known tissue types (e.g., bone, fat, bladder, etc.) that have a known average SoS, and performs SoS parameter selection based on training data that includes precomputed images and SoS values and outputs a SoS matrix that is fine-tuned for the tissue type being examined.

In some embodiments, the machine-learned model 402 is configured to receive RF data 410 and one or more secondary inputs 411, such as, for example, a default SoS matrix (e.g., having all values set to 1540 m/s), a region of interest, a label for an anatomy (e.g., cardiac), an examination type, an indicator of the type of ultrasound probe, the ultrasound frequency, combinations thereof, and the like. In response to these inputs, machine-learned model 402 generates SoS matrix 413.

Thus, while the raw (unprocessed) RF data is being used to generate an ultrasound image, the RF data is being maintained and being interpreted beyond that which is seen in the ultrasound image. That is, information is being gathered from the RF data that wouldn't necessarily be appreciated or observed in the ultrasound image in real-time. In some instances, this extra information includes, but is not limited to, phase and frequency information in the RF data (that is not part of the ultrasound image that is generated). In some embodiments, the information is processed to produce usable values that are output to the user. For example, the RF data can be processed to extract and reveal certain deep cellular details (e.g., cell makeup, cell stiffness, cell death as part of a processed referred to as epistasis, disease, repair, etc.). The processed data can be formatted as an image (e.g., an overlay that is placed on or over another image, or portion thereof, etc.). For example, such an image can include areas (e.g., pixels) of different colors based on differences in the data (e.g., differences in the raw RF data, differences in the SoS, etc.). This type of image, or color coded map (e.g., a mapping of the SoS), can be particularly value, such as when, for example, an organ (e.g., a liver) has a an expected or typical SoS yet a portion of the organ has a SoS that is different than the expected or typical SoS, which could be valuable information (e.g., diagnostic information) to know. The processing of data can be done by a computing device, and that computing device can include machine-learned models, including those machined-learned models described herein.

Example Procedures

Figure 10:
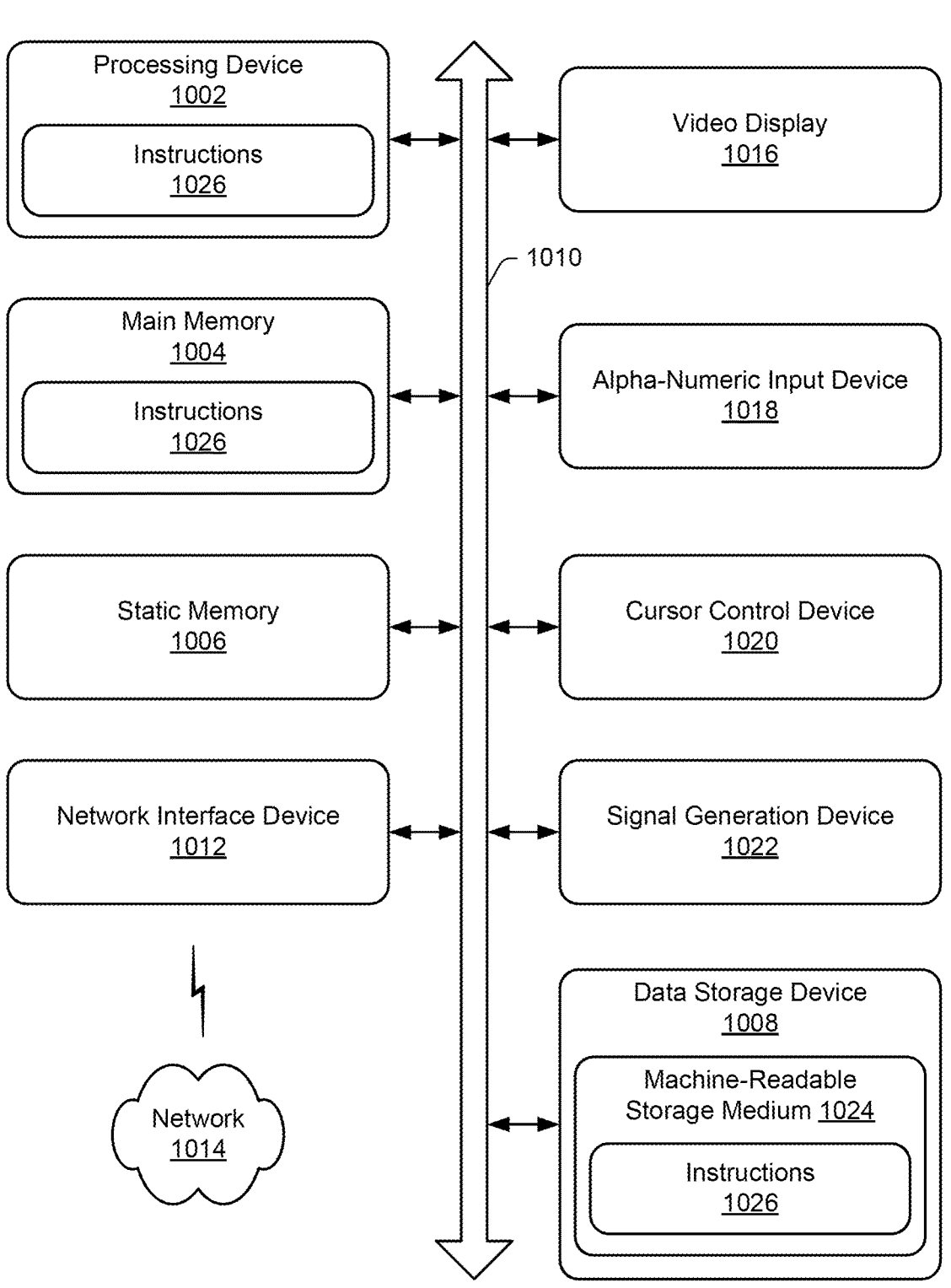
FIG. 10 illustrates a block diagram of an example computing device that can perform one or more of the operations described herein, in accordance with some embodiments.

FIG. 5 illustrates an example method 500 that can be implemented by an ultrasound system in accordance with some embodiments. The ultrasound system can include an ultrasound probe (e.g., an ultrasound scanner with a transducer array), one or more analog-to-digital converters, a beamformer, a processor system, an image generation circuit, a display device, and a memory. In some embodiments, the ultrasound system includes a computing device having processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem. In some embodiments, the computing device is represented by a computing device as shown in FIG. 10.

Ultrasound is transmitted at a patient anatomy and ultrasound reflections are received from the patient anatomy (block 502). For example, an ultrasound probe can transmit the ultrasound and receive the reflections. Sampled data is generated based on the ultrasound reflections (block 504). For example, one or more analog-to-digital converters can generate the sampled data. A beamformer beamforms the sampled data using delay values determined from speed-of-sound values (block 506). Ultrasound images are generated based on the sampled data and candidate sound speeds (block 508). Image scores are generated for the ultrasound images (block 510). Speed-of-sound values are determined from the candidate sound speeds based on a ranking of the ultrasound images according to the image scores (block 512). For example, a processor system can generate the ultrasound images and image scores and determine the speed-of-sound values.

In some embodiments, the processor system implements an ultrasound system emulator to generate the ultrasound images, and a machine-learned model to generate the image scores. In some embodiments, the ultrasound system emulator can emulate, match, approximate, simulate, etc., beamforming and image generation functions of the ultrasound system. In some embodiments, the processor system can generate the image scores based on a contrast level of the ultrasound images.

In some embodiments, an image generation circuit generates an ultrasound image from outputs of the beamformer, and a display device displays the ultrasound image. The processor system can adjust at least one of the candidate sound speeds based on the ultrasound image. In some embodiments, the adjustment is based on a difference of a pixel value in the ultrasound image and an expected pixel value (e.g., black and/or white values). In some embodiments, the one or more analog-to-digital converters generate the sampled data at a first bit precision for the generation of the ultrasound image and at a second bit precision for the generation of the ultrasound images. The first bit precision can be higher than the second bit precision. Alternatively, the first bit precision can be lower than the second bit precision.

In some embodiments, the speed-of-sound values include a speed-of-sound value for each line of the ultrasound transmitted by the ultrasound probe. In some embodiments, the speed-of-sound value for one line of the ultrasound is based on the speed-of-sound value for another line. For example, an offset can be applied to the speed-of-sound value for the other line to generate the speed-of-sound value for the one line. Additionally or alternatively, the speed-of-sound value for the one line can be determined by interpolating the speed-of-sound values for other lines.

In some embodiments, an AI model trained to segment specific anatomy, for example, liver, bone, skin line, kidney, is used to first identify different anatomy and tissue structure. Following this, a lookup table can be used to match this anatomy with known SoS values previously determined by other means. In some embodiments, these values are used to adjust the initial SoS values per sample and the beamforming adjusted accordingly. The estimated SoS values can be used directly or as initial estimates to more detailed SoS value search as already described.

In some embodiments, an AI model is trained directly to generate SoS values per pixel from the source data itself. For example, using previously computed SoS value image pairs, the AI model can be used to either compute SoS per pixel (sample and line) which is used directly by the beamformer or as initial estimates to a more detailed SoS value search as already described.

In some embodiments, a memory (e.g., a database) maintains candidate sound speeds. The memory can maintain candidate sound speeds for different patient anatomies, ultrasound probes, examination types, ultrasound frequencies, etc. Hence, the candidate sound speeds can be obtained from the memory based on the patient anatomy or a property of the ultrasound probe, such as the ultrasound probe's manufacturer or ultrasound frequency used.

FIG. 6 illustrates an example method 600 that can be implemented by an ultrasound system in accordance with the present invention. The ultrasound system can include an ultrasound probe (e.g., an ultrasound scanner with a transducer array), one or more analog-to-digital converters, a beamformer, a processor system, an image generation circuit, a display device, and a memory. In some embodiments, the ultrasound system includes a computing device having processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem. In some embodiments, the computing device is represented by a computing device as shown in FIG. 10.

Ultrasound is transmitted at a patient anatomy and ultrasound reflections are received from the patient anatomy as part of a current ultrasound examination (block 602). An ultrasound probe can transmit the ultrasound and received the ultrasound reflections. Sampled data is generated based on the ultrasound reflections (block 604). One or more analog-to-digital converters can generate the sampled data. A beamformer beamforms the sampled data using delay values (block 606). An ultrasound image is generated based on an output of the beamformer (block 608). An image generation circuit can generate the ultrasound image. A region of interest in the ultrasound image is determined (block 610). Candidate sound speeds for the region of interest are determined (block 612). Ultrasound images are generated based on the sampled data and the candidate sound speeds (block 614). The ultrasound images are ranked based on image scores for the ultrasound images (block 616). The delay values used by the beamformer are adjusted based on the candidate sound speeds and the ranking (block 618). In some embodiments, a processor system implements blocks 610-618.

In some embodiments, the processor system implements a machine-learned model to determine the region of interest, and the region of interest includes the patient anatomy. In some embodiments, the image scores are generated based on image content inside the region of interest and not based on image content outside the region of interest.

In some embodiments, a display device displays a user interface configured to display the ultrasound image and receive a user selection. The region of interest can be determined based on the user selection. For instance, a user can trace on the user interface an outline of the region of interest. Note also that this process as well as other processes described herein can be performed for different regions of interest. For example, because the raw (unprocessed) RF data is stored and maintained, such data can be processed for different regions of interest at the same or different times.

In some embodiments, a memory maintains speeds of sound. In some embodiments the delay values used by the beamformer prior to the adjustment are based on the speeds of sound from the memory that were determined as part of a previous ultrasound examination.

In some embodiments, based on the ultrasound and the ultrasound reflections, an initial speed-of-sound value is generated, and the delay values used by the beamformer prior to the adjustment are based on the initial speed-of-sound value. In some embodiments, the initial speed-of-sound value is determined by a direct estimation, such as with a machine-learned model or by using pulse-echo ultrasound, as previously described. Additionally or alternatively, the delay values used by the beamformer prior to the adjustment can be based on a default speed-of-sound value, such as a value of 1540 m/s that is stored in the memory under a default values register setting.

In some embodiments, a display device displays a user interface configured to receive a user selection for enablement of speed of sound compensation. In some embodiments, the adjustment of the delay values used by the beamformer is enabled responsive to the user selection.

FIG. 7 illustrates an example method 700 that can be implemented by an ultrasound system in accordance with the present invention. The ultrasound system can include an ultrasound probe (e.g., an ultrasound scanner with a transducer array), one or more analog-to-digital converters, a beamformer, a processor system, an image generation circuit, a display device, and a memory. In some embodiments, the ultrasound system includes a computing device having processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem. In some embodiments, the computing device is represented by a computing device as shown in FIG. 10.

Ultrasound is transmitted at a patient anatomy and ultrasound reflections are received from the patient anatomy (block 702). For example, an ultrasound probe can transmit the ultrasound and receive the ultrasound reflections. Sampled data based on the ultrasound reflections is generated (block 704). For example, one or more analog-to-digital converters can generate the sampled data. A machine-learned model generates, based on the sampled data, an array of speed-of-sound values (block 706). A processor system can implement the machine-learned model. The machine-learned model can include one or more neural networks to generate the array of speed-of-sound values. The SoS matrix in FIG. 4 is an example of the array of speed-of-sound values. Delay values are determined from the array of speed-of-sound values (block 708). A beamformer is configured with the delay values to beamform the sampled data (block 710). An ultrasound image is generated based on an output of the beamformer configured with the delay values (block 712).

Example Machine-Learned Models

Many of the aspects described herein can be implemented using a machine-learned model. For the purposes of this disclosure, a machine-learned model is any model that accepts an input, analyzes and/or processes the input based on an algorithm derived via machine-learning training, and provides an output. A machine-learned model can be conceptualized as a mathematical function of the following form:

$$f(\hat{s}, \theta) = \hat{y} \qquad \text{Equation (1)}$$

In Equation (1), the operator f represents the processing of the machine-learned model based on an input and providing an output. The term $\hat{s}$ represents a model input, such as ultrasound data. The model analyzes/processes the input $\hat{s}$ using parameters $\theta$ to generate output $\hat{y}$ (e.g., object identification, object segmentation, object classification, etc.). Both § and § can be scalar values, matrices, vectors, or mathematical representations of phenomena such as categories, classifications, image characteristics, the images themselves, text, labels, or the like. The parameters $\theta$ can be any suitable mathematical operations, including but not limited to applications of weights and biases, filter coefficients, summations or other aggregations of data inputs, distribution parameters such as mean and variance in a Gaussian distribution, linear algebra-based operators, or other parameters, including combinations of different parameters, suitable to map data to a desired output.

Figure 8:
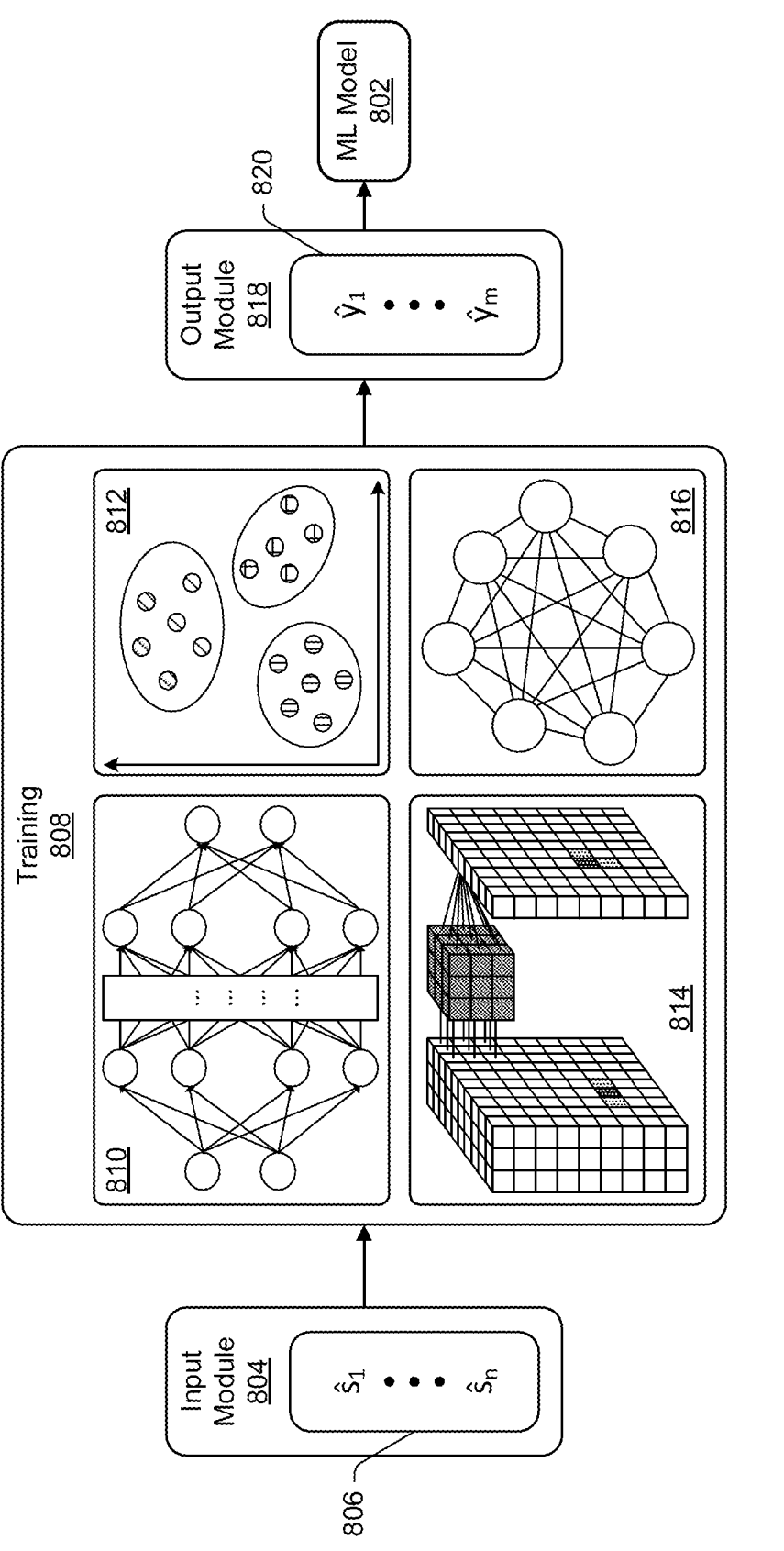
FIG. 8 represents an example machine-learning architecture for training a machine-learned model.

FIG. 8 represents an example machine-learning architecture 800 used to train a machine-learned model M 802 (e.g., machine-learned models 210, 310, and 402). Referring to FIG. 8, an input module 804 accepts an input $\hat{s}$ 806, which can be an array with members $\hat{s}_1$ through $\hat{s}n$. The input s 806 is fed into a training module 808, which processes the input s 806 based on the machine-learning architecture 800. For example, if the machine-learning architecture 800 uses a multilayer perceptron (MLP) model 810, the training module 808 applies weights and biases to the input $\hat{s}$ 806 through one or more layers of perceptrons, each perceptron performing a fit using its own weights and biases according to its given functional form. MLP weights and biases can be adjusted so that they are optimized against a least mean square, logcosh, or other optimization function (e.g., loss function) known in the art. Although an MLP model 810 is described here as an example, any suitable machine-learning technique can be employed, some examples of which include but are not limited to k-means clustering 812, convolutional neural networks (CNN) 814, a Boltzmann machine 816, Gaussian mixture models (GMM), and long short-term memory (LSTM). The training module 808 provides an input to an output module 818. The output module 818 analyzes the input from the training module 808 and provides an output in the form of $\hat{y}$ 820, which can be an array with members $\hat{y}_1$ through $\hat{y}_m$. The output 820 can represent a known correlation with the input $\hat{s}$ 806, such as, for example, object identification, segmentation, and/or classification.

In some examples, the input $\hat{s}$ 806 can be a training input labeled with known output correlation values, and these known values can be used to optimize the output $\hat{y}$ 820 in training against the optimization/loss function. In other examples, the machine-learning architecture 800 can categorize the output $\hat{y}$ 820 values without being given known correlation values to the inputs $\hat{s}$ 806. In some examples, the machine-learning architecture 800 can be a combination of machine-learning architectures. By way of example, a first network can use the input s 806 and provide the output $\hat{y}$ 820 as an input $\hat{s}_{ML}$ to a second machine-learned architecture, with the second machine-learned architecture providing a final output $\hat{y}_f$. In another example, one or more machine-learning architectures can be implemented at various points throughout the training module 808.

In some machine-learned models, all layers of the model are fully connected. For example, all perceptrons in an MLP model act on every member of s. For an MLP model with a 100×100 pixel image as the input, each perceptron provides weights/biases for 10,000 inputs. With a large, densely layered model, this may result in slower processing and/or issues with vanishing and/or exploding gradients. A CNN, which may not be a fully connected model, can process the same image using 5×5 tiled regions, requiring only 25 perceptrons with shared weights, giving much greater efficiency than the fully connected MLP model.

Figure 9:
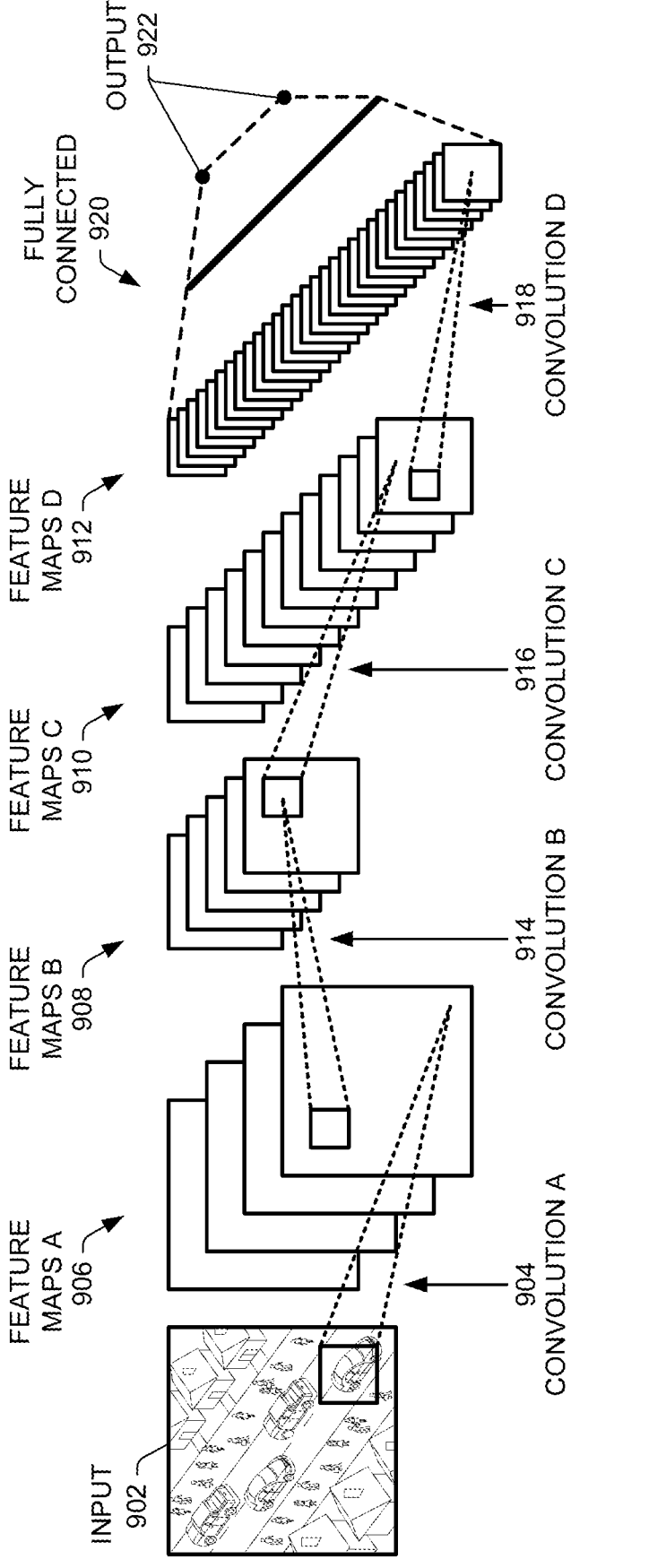
FIG. 9 represents an example model using a convolutional neural network (CNN) to process an input image that includes representations of objects that can be identified via object recognition.

FIG. 9 represents an example model 900 using a CNN to process an input image 902, which includes representations of objects that can be identified via object recognition, such as people or cars (or an anatomy). Convolution A 904 can be performed to create a first set of feature maps (e.g., feature maps A 906). A feature map can be a mapping of aspects of the input image 902 given by a filter element of the CNN. This process can be repeated using feature maps A 906 to generate further feature maps B 908, feature maps C 910, and feature maps D 912 using convolution B 914, convolution C 916, and convolution D 918, respectively. In this example, the feature maps D 912 become an input for fully connected network layers 920. In this way, the machine-learned model can be trained to recognize certain elements of the image, such as people, cars, or a particular patient anatomy, and provide an output 922 that, for example, identifies the recognized elements. In some aspects, the secondary input in FIG. 4 can be appended to a feature map (e.g., feature map B 908) generated by a neural network (e.g., CNN).

Although the example of FIG. 9 shows a CNN as a part of a fully connected network, other architectures are possible and this example should not be seen as limiting. There can be more or fewer layers in the CNN. A CNN component for a model can be placed in a different order, or the model can contain additional components or models. There may be no fully connected components, such as a fully convolutional network. Additional aspects of the CNN, such as pooling, downsampling, upsampling, or other aspects known to people skilled in the art can also be employed.

Example Device

FIG. 10 illustrates a block diagram of an example computing device 1000 that can perform one or more of the operations described herein, in accordance with some implementations. The computing device 1000 can be connected to other computing devices in a local area network (LAN), an intranet, an extranet, and/or the Internet. The computing device can operate in the capacity of a server machine in a client-server network environment or in the capacity of a client in a peer-to-peer network environment. The computing device can be provided by a personal computer (PC), a server computer, a desktop computer, a laptop computer, a tablet computer, a smartphone, an ultrasound machine, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein. In some implementations, the computing device 1000 is one or more of an ultrasound machine, an ultrasound scanner, an access point, and a display device.

Referring to FIG. 10, the example computing device 1000 can include a processing device 1002 (e.g., a general-purpose processor, a programmable logic device (PLD), etc.), a main memory 1004 (e.g., synchronous dynamic random-access memory (DRAM), read-only memory (ROM), etc.), and a static memory 1006 (e.g., flash memory, a data storage device 1008, etc.), which can communicate with each other via a bus 1010. The processing device 1002 can be provided by one or more general-purpose processing devices such as a microprocessor, a central processing unit, or the like. In an illustrative example, the processing device 1002 comprises a complex instruction set computing (CISC) microprocessor, a reduced instruction set computing (RISC) microprocessor, a very long instruction word (VLIW) microprocessor, or a processor implementing other instruction sets or processors implementing a combination of instruction sets. The processing device 1002 can also comprise one or more special-purpose processing devices such as an application-specific integrated circuit (ASIC), a field programmable gate array (FPGA), a digital signal processor (DSP), a network processor, or the like. The processing device 1002 can be configured to execute the operations described herein, in accordance with one or more aspects of the present disclosure, for performing the operations and steps discussed herein.

The computing device 1000 can further include a network interface device 1012, which can communicate with a network 1014. The computing device 1000 also can include a video display unit 1016 (e.g., a liquid crystal display (LCD), an organic light-emitting diode (OLED), a cathode ray tube (CRT), etc.), an alphanumeric input device 1018 (e.g., a keyboard), a cursor control device 1020 (e.g., a mouse), and an acoustic signal generation device 1022 (e.g., a speaker, a microphone, etc.). In one embodiment, the video display unit 1016, the alphanumeric input device 1018, and the cursor control device 1020 can be combined into a single component or device (e.g., an LCD touch screen).

The data storage device 1008 can include a computer-readable storage medium 1024 on which can be stored one or more sets of instructions 1026 (e.g., instructions for carrying out the operations described herein, in accordance with one or more aspects of the present disclosure). The instructions 1026 can also reside, completely or at least partially, within the main memory 1004 and/or within the processing device 1002 during execution thereof by the computing device 1000, where the main memory 1004 and the processing device 1002 also constitute computer-readable media. The instructions can further be transmitted or received over the network 1014 via the network interface device 1012.

Various techniques are described in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. In some aspects, the modules described herein are embodied in the data storage device 1008 of the computing device 1000 as executable instructions or code. Although represented as software implementations, the described modules can be implemented as any form of a control application, software application, signal-processing and control module, hardware, or firmware installed on the computing device 1000.

While the computer-readable storage medium 1024 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding, or carrying a set of instructions for execution by the machine and that causes the machine to perform the methods described herein. The term "computer-readable storage medium" shall accordingly be taken to include, but not be limited to, solid-state memories, optical media, and magnetic media.

Aspects Other than Speed-of-Sound

In addition to the SoS examples disclosed herein, the techniques disclosed herein can be used for selection and estimation of various ultrasound parameters using RF data.

Figure 11:
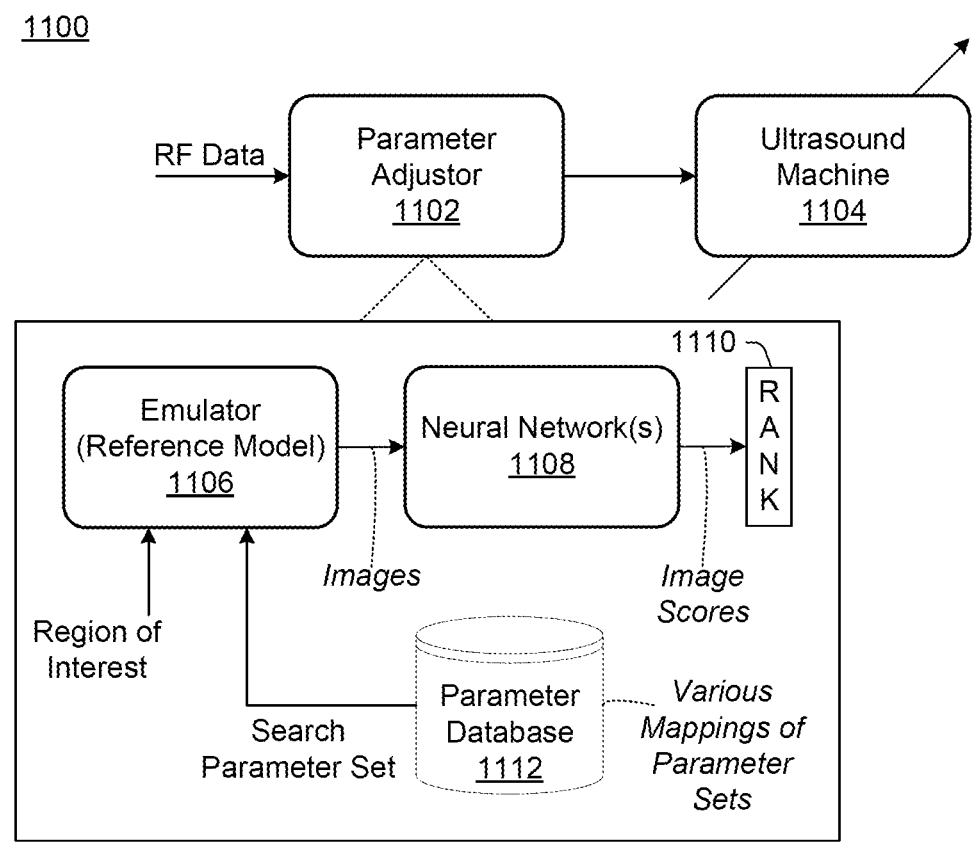
FIG. 11 illustrates a data flow diagram of a process for ultrasound imaging parameter selection in accordance with some embodiments.

FIG. 11 illustrates at 1100 ultrasound imaging parameter selection in accordance with the present invention. Examples of ultrasound imaging parameters that can be determined according to the present invention include gain, depth, preset (e.g., examination type), and the like. Referring to FIG. 11, the system at 1100 includes a parameter adjustor block 1102 and an ultrasound machine 1104. In some embodiments, the parameter adjustor block 1102 illustrated in FIG. 11 includes an emulator 1106, one or more neural networks 1108, a rank block 1110, and a parameter database 1112. The emulator 1106 can function similar to the emulator 208 as previously described. For example, the emulator 1106 can include any suitable function in hardware, software, firmware, GPU, or combinations thereof, such as beamforming and image generation functions of an ultrasound system. In some embodiments, the emulator 1106 receives a region of interest for an ultrasound image, and the region of interest can be automatically determined (e.g., a machine-learned model) or user-selected. The parameter database 1112 maintains various combinations of ultrasound imaging parameters, which are supplied to the emulator 1106 for image generation. In some embodiments, the emulator 1106 generates ultrasound images from the RF data using the ultrasound imaging parameters from the parameters database 1112. For instance, one image can correspond to a first gain setting, and another image can correspond to another gain setting. In some embodiments, one image can correspond to a first gain setting and a first depth setting, and another image can correspond to another gain setting and another depth setting.

In some embodiments, the images generated by the emulator 1106 are processed by the neural network 1108, which generates image quality scores, in a similar fashion to the neural network 210 in FIG. 2. In some embodiments, the images are ranked according to their scores by the rank function 1110. The parameters for a highest scoring image are transferred from the parameter adjustor block 1102 to the ultrasound machine 1104, which can in turn generate ultrasound images for an ultrasound examination under the configuration determined by the parameter adjustor block 1102. Hence, the image quality is improved compared to the original setting of the ultrasound machine 1104.

Figure 12:
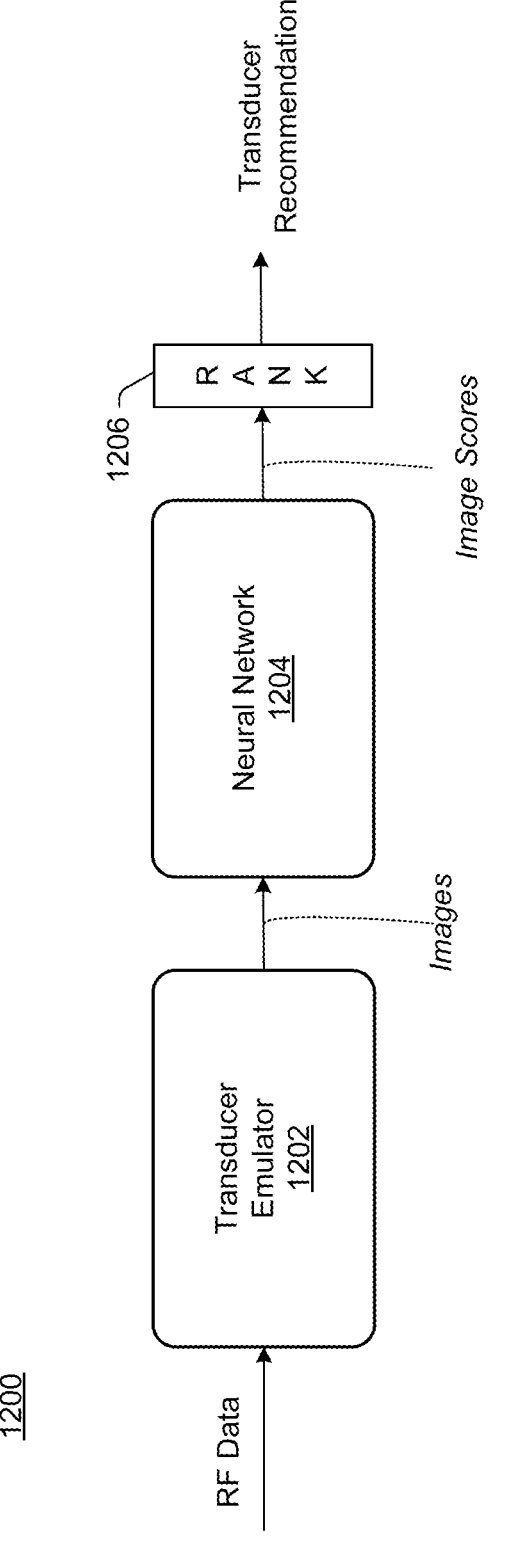
FIG. 12 illustrates a data flow diagram of a process for ultrasound probe emulation and recommendation in accordance some embodiments.

In some embodiments, the techniques disclosed herein are used for transducer (e.g., ultrasound probe or ultrasound scanner) recommendation based on the RF data. FIG. 12 illustrates at 1200 ultrasound probe emulation and recommendation in accordance with the present invention. Referring to FIG. 12, in some embodiments, the system at 1200 includes a transducer emulator 1202, one or more neural networks 1204 (or any suitable machine-learned models), and a rank function 1206. The transducer emulator 1202 can include any suitable machine-learned model and/or circuitry and/or processing functions to generate, based on the RF data captured with a first transducer, an image having a style as if it were captured with a second transducer. For example, the transducer emulator 1202 can color the RF data to match in any suitable way, (e.g., to match statistics), upsample data, applying transfer functions, etc., as if the data was generated by a different transducer or ultrasound probe. As an example, the RF data could be collected using an ultrasound probe with a transducer operating at a first frequency, and the transducer emulator 1202 can color the data and generate images to appear as if the transducer was operating at a second frequency. In some embodiments, the RF data is collected using an ultrasound probe with a first type of transducer array (e.g., linear, 1.5 D, phased, etc.), and the transducer emulator 1202 colors the data and generates images to appear as if the ultrasound probe had a second type of transducer array (e.g., 1.75D).

In some embodiments, the neural network 1204 generates image scores for the images generated by the transducer emulator 1202, similar to the neural network 210 in FIG. 2. In some embodiments, the rank function 1206 ranks the images generated by the transducer emulator 1202 according to the ranking by the rank function 1206, and the system at 1200 can present a recommendation to a user for a transducer (e.g., ultrasound probe) based on the ranking. For instance, the transducer being emulated by the transducer emulator 1202 that results in the highest image score can be recommended to the clinician for the ultrasound examination. The recommendation can be displayed in a user interface of an ultrasound machine (not shown in FIG. 12).

In some embodiments, the techniques disclosed herein are used for noise power estimation based on the RF data. Since the RF data has not been processed (e.g., decimated, filtered, etc.), the RF data maintains the maximum information-theoretic value. Hence, using it to estimate noise power (or signal to noise ratio) can produce better estimates than using data that has already been processed, e.g., beamformed. In some embodiments, the noise power estimate are used to set parameters for processing in the transceiver, including beamformer parameters and gains. In some embodiments, the noise power estimates are also be used to identify a faulty transducer element, and to generate new line data when the noise power exceeds a threshold. The new line data can be generated from other line data, such as by interpolating from adjacent lines.

The systems, devices, and methods described herein constitute numerous advantages compared to conventional systems, devices, and methods. For example, the use of captured RF data prior to beamforming has maximum information-theoretic value, facilitating better and faster parameter estimation compared to the use of beamformed data. The RF data can be processed in real time so that results can be used in a current ultrasound examination. The invention is applicable to both pre-clinical and clinical systems and can be used for a wide variety of parameter selection and estimation, including image-wide speed-of-sound estimation, noise-power estimation and beamformer control therefrom, imaging-parameter estimation, and transducer emulation and recommendation.

There are a number of example embodiments described herein.

Example 1 is an ultrasound system comprising: an ultrasound probe configured to transmit ultrasound at a patient anatomy and receive ultrasound reflections from the patient anatomy; one or more analog-to-digital converters configured to generate sampled data based on the ultrasound reflections; a beamformer configured to beamform the sampled data using delay values determined from speed-of-sound values; and a processor system. The process system is implemented to: generate ultrasound images based on the sampled data and candidate sound speeds; generate image scores for the ultrasound images; and determine the speed-of-sound values from the candidate sound speeds based on a ranking of the ultrasound images according to the image scores.

Example 2 is the ultrasound system of example 1 that may optionally include that the processor system implements: an ultrasound system emulator to generate the ultrasound images; and a machine-learned model to generate the image scores.

Example 3 is the ultrasound system of example 1 that may optionally include that the processor system is implemented to generate the image scores based on a contrast level of the ultrasound images.

Example 4 is the ultrasound system of example 1 that may optionally include an image generation circuit implemented to generate an ultrasound image from outputs of the beamformer and a display device implemented to display the ultrasound image.

Example 5 is the ultrasound system of example 4 that may optionally include that the processor system is implemented to adjust at least one of the candidate sound speeds based on the ultrasound image.

Example 6 is the ultrasound system of example 5 that may optionally include that the processor system is configured to adjust the at least one of the candidate sound speeds based on a difference of a pixel value in the ultrasound image and an expected pixel value.

Example 7 is the ultrasound system of example 4 that may optionally include that the one or more analog-to-digital converters are implemented to generate the sampled data at a first bit precision for the generation of the ultrasound image and at a second bit precision for the generation of the ultrasound images.

Example 8 is the ultrasound system of example 1 that may optionally include that the speed-of-sound values include a speed-of-sound value for each line of the ultrasound transmitted by the ultrasound probe.

Example 9 is the ultrasound system of example 8 that may optionally include that the processor system is implemented to determine the speed-of-sound value for one line of the ultrasound based on the speed-of-sound value for another line.

Example 10 is the ultrasound system of example 1 that may optionally include a memory implemented to maintain the candidate sound speeds, wherein the processor system is implemented to obtain the candidate sound speeds from the memory based on the patient anatomy.

Example 11 is the ultrasound system of example 1 that may optionally include a memory implemented to maintain the candidate sound speeds, wherein the processor system is implemented to obtain the candidate sound speeds from the memory based on a property of the ultrasound probe.

Example 12 is ultrasound system comprising: an ultrasound probe configured to transmit ultrasound at a patient anatomy and receive ultrasound reflections from the patient anatomy as part of a current ultrasound examination; one or more analog-to-digital converters configured to generate sampled data based on the ultrasound reflections; a beamformer configured to beamform the sampled data using delay values; an image generation circuit configured to generate an ultrasound image based on an output of the beamformer; and a processor system. The processor system is implemented to: determine a region of interest in the ultrasound image; determine candidate sound speeds for the region of interest; generate ultrasound images based on the sampled data and the candidate sound speeds; rank the ultrasound images based on image scores for the ultrasound images; and adjust the delay values used by the beamformer based on the candidate sound speeds and the ranking.

Example 13 is the ultrasound system of example 12 that may optionally include that the processor system implements a machine-learned model to determine the region of interest, and the region of interest includes the patient anatomy.

Example 14 is the ultrasound system of example 12 that may optionally include a display device implemented to display a user interface configured to display the ultrasound image and receive a user selection, wherein the processor system is implemented to determine the region of interest based on the user selection.

Example 15 is the ultrasound system of example 12 that may optionally include a memory implemented to maintain speeds of sound, wherein the processor system is implemented to determine the delay values used by the beamformer prior to the adjustment based on the speeds of sound from the memory determined as part of a previous ultrasound examination.

Example 16 is the ultrasound system of example 12 that may optionally include that the processor system is implemented to generate, based on the ultrasound and the ultrasound reflections, an initial speed-of-sound value, wherein the delay values used by the beamformer prior to the adjustment are based on the initial speed-of-sound value.

Example 17 is the ultrasound system of example 12 that may optionally include that the delay values used by the beamformer prior to the adjustment are based on a default speed-of-sound value.

Example 18 is the ultrasound system of example 12 that may optionally include that the processor system is implemented to generate the image scores based on image content inside the region of interest and not based on image content outside the region of interest.

Example 19 is the ultrasound system of example 12 that may optionally include a display device implemented to display a user interface configured to receive a user selection for enablement of speed of sound compensation, wherein the processor system is implemented to enable the adjustment of the delay values used by the beamformer responsive to the user selection.

Example 20 is an ultrasound system comprising: an ultrasound probe configured to transmit ultrasound at a patient anatomy and receive ultrasound reflections from the patient anatomy; one or more analog-to-digital converters configured to generate sampled data based on the ultrasound reflections; and a processor system. The processor system is configured to: implement a machine-learned model to generate, based on the sampled data, an array of speed-of-sound values; determine delay values from the array of speed-of-sound values; and configure a beamformer with the delay values to beamform the sampled data. The processor system also includes an image generation circuit implemented to generate an ultrasound image based on an output of the beamformer configured with the delay values.

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in some embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

We claim:

1. An ultrasound system comprising:

an ultrasound probe configured to transmit ultrasound at a patient anatomy and receive ultrasound reflections from the patient anatomy;

one or more analog-to-digital converters configured to generate sampled data based on the ultrasound reflections;

a beamformer configured to beamform the sampled data using delay values determined from speed-of-sound values; and a processor system implemented to:

generate ultrasound images based on the sampled data and candidate sound speeds;

generate image scores for the ultrasound images; and determine the speed-of-sound values from the candidate sound speeds based on a ranking of the ultrasound images according to the image scores, wherein the speed-of-sound values include multiple speed-of-sound values, determined on an individual line basis, for individual lines of the ultrasound transmitted by the ultrasound probe, wherein the candidate sound speeds include adjusted speed of sounds values generated by a first machine-learned model implemented by the processor system based on predetermined speed of sound values and ultrasound image data.

2. The ultrasound system as described in claim 1, wherein the processor system implements:

an ultrasound system emulator to generate the ultrasound images; and a second machine-learned model to generate the image scores.

3. The ultrasound system as described in claim 1, wherein the processor system is implemented to generate the image scores based on a contrast level of the ultrasound images.

4. The ultrasound system as described in claim 1, further comprising:

an image generation circuit implemented to generate an ultrasound image from outputs of the beamformer; and a display device implemented to display the ultrasound image.

5. The ultrasound system as described in claim 4, wherein the processor system is implemented to adjust at least one of the candidate sound speeds based on the ultrasound image.

6. The ultrasound system as described in claim 5, wherein the processor system is configured to adjust the at least one of the candidate sound speeds based on a difference of a pixel value in the ultrasound image and an expected pixel value.

7. The ultrasound system as described in claim 4, wherein the one or more analog-to-digital converters are implemented to generate the sampled data at a first bit precision for the generation of the ultrasound image and at a second bit precision for the generation of the ultrasound images.

8. The ultrasound system as described in claim 1, wherein the speed-of-sound values include a speed-of-sound value for each line of the ultrasound transmitted by the ultrasound probe.

9. The ultrasound system as described in claim 1, wherein the processor system is implemented to determine the speed-of-sound value for one line of the ultrasound based on the speed-of-sound value for another line.

10. The ultrasound system as described in claim 1, further comprising a memory implemented to maintain the candidate sound speeds, wherein the processor system is implemented to obtain the candidate sound speeds from the memory based on the patient anatomy.

11. The ultrasound system as described in claim 1, further comprising a memory implemented to maintain the candidate sound speeds, wherein the processor system is implemented to obtain the candidate sound speeds from the memory based on a property of the ultrasound probe.

12. An ultrasound system comprising:

an ultrasound probe configured to transmit ultrasound at a patient anatomy and receive ultrasound reflections from the patient anatomy as part of a current ultrasound examination;

one or more analog-to-digital converters configured to generate sampled data based on the ultrasound reflections;

a beamformer configured to beamform the sampled data using delay values;

an image generation circuit configured to generate an ultrasound image based on an output of the beamformer; and a processor system implemented to:

determine a region of interest in the ultrasound image;

determine candidate sound speeds for the region of interest, wherein the candidate sound speeds are determined from speed-of-sound values that multiple speed-of-sound values, determined on an individual line basis, for individual lines of the ultrasound transmitted by the ultrasound probe, wherein the candidate sound speeds include adjusted speed of sounds values generated by a first machine-learned model implemented by the processor system based on predetermined speed of sound values and ultrasound image data;

generate ultrasound images based on the sampled data and the candidate sound speeds;

rank the ultrasound images based on image scores for the ultrasound images; and adjust the delay values used by the beamformer based on the candidate sound speeds and the ranking.

13. The ultrasound system as described in claim 12, wherein the processor system implements a machine-learned model to determine the region of interest, and the region of interest includes the patient anatomy.

14. The ultrasound system as described in claim 12, further comprising a display device implemented to display a user interface configured to display the ultrasound image and receive a user selection, wherein the processor system is implemented to determine the region of interest based on the user selection.

15. The ultrasound system as described in claim 12, further comprising a memory implemented to maintain speeds of sound, wherein the processor system is implemented to determine the delay values used by the beamformer prior to the adjustment based on the speeds of sound from the memory determined as part of a previous ultrasound examination.

16. The ultrasound system as described in claim 12, wherein the processor system is implemented to generate, based on the ultrasound and the ultrasound reflections, an initial speed-of-sound value, wherein the delay values used by the beamformer prior to the adjustment are based on the initial speed-of-sound value.

17. The ultrasound system as described in claim 12, wherein the delay values used by the beamformer prior to the adjustment are based on a default speed-of-sound value.

18. The ultrasound system as described in claim 12, wherein the processor system is implemented to generate the image scores based on image content inside the region of interest and not based on image content outside the region of interest.

19. The ultrasound system as described in claim 12, further comprising a display device implemented to display a user interface configured to receive a user selection for enablement of speed of sound compensation, wherein the processor system is implemented to enable the adjustment of the delay values used by the beamformer responsive to the user selection.

20. An ultrasound system comprising:

an ultrasound probe configured to transmit ultrasound at a patient anatomy and receive ultrasound reflections from the patient anatomy;

one or more analog-to-digital converters configured to generate sampled data based on the ultrasound reflections;

a processor system configured to:

implement a machine-learned model to generate, based on the sampled data, an array of speed-of-sound values by adjusting predetermined candidate speed of sound based ultrasound image data, wherein the speed-of-sound values include multiple speed-of-sound values, determined on an individual line basis, for individual lines of the ultrasound transmitted by the ultrasound probe;

determine delay values from the array of speed-of-sound values; and configure a beamformer with the delay values to beam-form the sampled data; and an image generation circuit implemented to generate an ultrasound image based on an output of the beamformer configured with the delay values.

* * * * *